US011963905B2

(12) United States Patent
Comander et al.

(10) Patent No.: US 11,963,905 B2
(45) Date of Patent: *Apr. 23, 2024

(54) METHODS OF DELIVERING AN AGENT TO THE EYE

(71) Applicant: Massachusetts Eye and Ear Infirmary, Boston, MA (US)

(72) Inventors: Jason Comander, Boston, MA (US); Dean Eliott, Boston, MA (US); Leo Kim, Boston, MA (US); Luk H. Vandenberghe, Weston, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 623 days.

This patent is subject to a terminal disclaimer.

(21) Appl. No.: 17/140,505

(22) Filed: Jan. 4, 2021

(65) Prior Publication Data

US 2021/0196508 A1   Jul. 1, 2021

Related U.S. Application Data

(63) Continuation of application No. 15/572,274, filed as application No. PCT/US2016/031218 on May 6, 2016, now Pat. No. 10,881,548.

(60) Provisional application No. 62/158,393, filed on May 7, 2015.

(51) Int. Cl.
| A61F 9/007 | (2006.01) |
| A61F 9/00 | (2006.01) |
| A61K 31/573 | (2006.01) |
| A61K 49/00 | (2006.01) |

(52) U.S. Cl.
CPC ........ *A61F 9/0008* (2013.01); *A61F 9/00736* (2013.01); *A61F 9/00727* (2013.01); *A61K 31/573* (2013.01); *A61K 49/0034* (2013.01); *A61K 49/006* (2013.01); *C12N 2750/14242* (2013.01)

(58) Field of Classification Search
CPC ............... A61F 9/0008; A61F 9/00736; A61F 9/00727; A61K 31/573; A61K 49/0034; A61K 49/006; C12N 2750/14242
See application file for complete search history.

(56) References Cited

U.S. PATENT DOCUMENTS

| 5,037,384 A | 8/1991 | Chang |
| 5,817,075 A | 10/1998 | Giungo |
| 7,906,111 B2 | 3/2011 | Wilson et al. |
| 9,782,232 B1 | 10/2017 | Papac |
| 2001/0014788 A1 | 8/2001 | Morris |
| 2004/0216750 A1 | 11/2004 | Snyder et al. |
| 2007/0028928 A1 | 2/2007 | Peyman |
| 2007/0225727 A1 | 9/2007 | Matsuhisa et al. |

(Continued)

FOREIGN PATENT DOCUMENTS

| JP | 2007-500518 | 1/2007 |
| WO | WO 2005/033321 | 4/2005 |

(Continued)

OTHER PUBLICATIONS

Notice of Acceptance in Australian Appln. No. 2021200707, dated Aug. 10, 2022, 4 pages.

(Continued)

*Primary Examiner* — Susan S Su
(74) *Attorney, Agent, or Firm* — Fish & Richardson P.C.

(57) ABSTRACT

Methods of delivering agents to structures within the eye are provided.

18 Claims, 6 Drawing Sheets

(56) References Cited

U.S. PATENT DOCUMENTS

| | | | |
|---|---|---|---|
| 2008/0090914 | A1 | 4/2008 | Enaida et al. |
| 2009/0226531 | A1 | 9/2009 | Lyons et al. |
| 2011/0098536 | A1 | 4/2011 | Corcosteugi et al. |
| 2012/0093772 | A1 | 4/2012 | Horsager et al. |
| 2014/0248231 | A1 | 9/2014 | Askari |
| 2015/0182756 | A1 | 7/2015 | Peyman |
| 2015/0283265 | A1 | 10/2015 | Peyman |
| 2015/0374543 | A1 | 12/2015 | Shapiro et al. |
| 2016/0296221 | A1 | 10/2016 | Morris |
| 2019/0254870 | A1 | 8/2019 | Hopkins |

FOREIGN PATENT DOCUMENTS

| | | |
|---|---|---|
| WO | WO 2006/110689 | 10/2006 |
| WO | WO 2014/160092 | 10/2014 |
| WO | WO 2015/054653 | 4/2015 |

OTHER PUBLICATIONS

Adachi et al., "MOLPHY: Programs for Molecular Phylogenetics based on Maximum Likelihood," Tokyo Institute of Statistical Mathematics, 1996, ed.
Altschul et al., "Gapped BLAST and PSI-BLAST: A new generation of protein database search programs," Nucleic Acids Res., 1997, 25:3389 3402.
American Society of Gene & Cell Therapy 17th Annual Meeting, Molecular Therapy, May 1, 2014, 22(Supplement 1): S1-S305.
Anisimova et al., "Approximate likelihood-ratio test for branches: A fast, accurate, and powerful alternative," Systematic Biology, 2006, 55:539-52.
AU Office Action in Australian Appln. No. 2016256894, dated Dec. 13, 2019, 3 pages.
Ausar et al., "Conformational stability and disassembly of Norwalk virus-like particles. Effect of pH and temperature," J. Biol. Chem., 2006, 281:19478-88.
Balazs et al., "Antibody-based protection against HIV infection by vectored immunoprophylaxis," Nature, 2012, 481:81-4.
Balazs et al., "Broad protection against influenza infection by vectored immunoprphylaxis in mice," Nat. Biotechnol., 2013, 31:647-52.
Bartel et al., "Directed evolution of novel adeno-associated viruses for therapeutic gene delivery," Gene Therapy, Mar. 2012, 19: 694-700.
Boutin et al., "Prevalence of serum IgG and neutralizing factors against AAV types 1, 2, 5, 6, 8 and 9 in the healthy population: implications for gene therapy using AAV vectors," Hum. Gene Ther., 2010, 21:704-12.
Calcedo et al. "Worldwide Epidemiology of Neutralizing Antibodies to Adeno-Associated Viruses," J. Infect. Dis., 2009, 199:381-90.
Cao et al., "Phylogenetic relationships among eutherian orders estimated from inferred sequences of mitochondrial proteins: instability of a tree based on a single gene, " J. Mol. Evol., 1994, 39:519-27.
Carvalho et al., "Abstract #: 120: Retinal Tropism of in Silico Reconstructed Ancestral Adeno-Associated Viruses, " Molecular Therapy, May 2014, 22(Supplement 1): S45.
Darriba et al., "ProTest3: Fast selection of best-fit models of protein evolution," Bioinformatics, 2011, 27(8):1164-5.
Dayhoff et al., "22 a model of evolutionary change in proteins." Atlas of protein sequence and structure. vol. 5. National Biomedical Research Foundation Silver Spring, 1978. 345-352.
Deal et al., "Vectored antibody gene delivery protects against plasmodium falciparum sporozoite challenge in mice," PNAS USA, 2014, 111:12528-32.
EBI Accession No. GSP:ANJ81137, "Adeno-associated viral capsid protein, AAV-8," Dec. 13, 2007.
Edgar, "MUSCLE: A multipole sequence alignment method with reduced time and space complexity," BMC Bioinform., 2004, 5:113.

EP European Search Report in Application No. 16790158.6, dated Jan. 3, 2019, 5 pages.
EP European Search Report in Application No. 18190809.6, dated Dec. 19, 2018, 5 pages.
EP Extended European Search Report in Application No. 16831443.3, dated Nov. 26, 2018, 20 pages.
Eyewiki.aao.org [online], "Pars Plana Vitrectomy," Nov. 20, 2019, retrieved on Mar. 27, 2020, retrieved from URL<https://eyewiki.aao.org/Pars_Plana_Vitrectomy>, 7 pages.
Felsenstein, "Maximum Likelihood and Minimum-Steps Methods for Estimating Evolutionary Trees from Data on Discrete Characters," Systematic Biology, 1973, 22:240-9.
Fisher et al., "Recombinant adeno-associated virus for muscle directed gene therapy," 1997, Nature Med., 3:306-12.
Gao et al., "Adeno-associated viruses undergo substantial evolution in primates during natural infections," PNAS, 2003, 100:6081-6.
Gao et al., "Clades of Adeno-associated viruses are widely disseminated in human tissues," J. Virol., 2004, 78:6381-88.
Gao et al., "New recombinant serotypes of AAV vectors," Current Gene Ther., 2005, 5:285-97.
Gascuel, "BioNJ: An improved version of the NJ algorithm based on a simple model of sequence data," Mol. Biol. Evol., 1997, 14:685-95.
GenBank Accession No. AAC03780.1, "major coat protein VP1 [Adeno-associated virus—2]," Feb. 24, 1998, 1 page.
GenBank Accession No. AAD13756.1, "capsid protein [Adeno-associated virus—5]," Feb. 10, 1999, 1 page.
GenBank Accession No. AAD27757.1, "capsid protein [Adeno-associated virus—1]," Apr. 27, 1999, 1 page.
GenBank Accession No. AAN03857.1, "capsid protein [Adeno-associated virus—8]," Sep. 2, 2002, 1 page.
GenBank Accession No. AAO88201.1, "capsid protein [Non-human primate Adeno-associated virus]," Apr. 9, 2003, 1 page.
GenBank Accession No. AAS99264.1, "capsid protein VP1 [Adeno-associated virus 9]," May 25, 2004, 1 page.
GenBank Accession No. EU368910.1, "Adeno-associated virus isolate AAV6.2 capsid protein VP1 gene, partial cds," Jul. 31, 2008, 1 page.
GenBank Accession No. EU368926, "Adeno-associated virus isolate rh32.33 capsid protein VP1 gene, partial cds," Jul. 31, 2008, 1 page.
Guindon et al., "New algorithms and methods to estimate maximum-likelihood phylogenies: assessing the performance of PhyML 3.0," System. Biol., 2010, 59:307-21.
Guindon et al., "A simple, fast, and accurate algorithm to estimate large phylogenies by maximum likelihood," Systematic Biology, 2003, 52:696-704.
Henikoff at al., "Amino acid substitution matrices from protein blocks, " PNAS, 1992, 89:10915-9.
Jones et al., "The rapid generation of mutation data matrices from protein sequences," 1992, Comp. Appl. Biosci., 8:275-82.
Katoh et al., "MAFFT version 5: Improvement in accuracy of multiple sequence alignment," Nuc. Acids Res., 2005, 33:511-8.
Koerber et al., "DNA Shuffling of Adeno-associated Virus Yields Functionally Diverse Viral Progeny," Molecular Therapy, Aug. 2008, 16: 1703-1709.
Lassmann et al., "Kalign, Kalignvu and Mumsa: Web servers for multiple sequence alignment," Nuc. Acids Res., 2006, 34:W596-99.
Limberis et al., "Intranasal antibody gene transfer in mice and ferrets elicits broad protection against pandemic influenza," Sci. Transl. Med., 2013, 5:187ra72.
Lock et al., "Rapid, simple, and versatile manufacturing of recombinant adeno-associated viral vectors at scale," Hum. Gene Ther., 2010, 21:1259-71.
Loytynoja et al., "An Algorithm for progressive multiple alignment of sequences with insertions," PNAS USA, 2005, 102:10557-62.
Loytynoja et al., "Phylogeny-Aware Gap Placement Prevents Errors in Sequence Alignment and Evolutionary Analysis," Science, 2008, 320:1632-5.
Maheshri et al., "Directed evolution of adeno-associated virus yields enhanced gene delivery vectors," Nature Biotechnology, Jan. 2006, 24: 198-204.

(56) References Cited

OTHER PUBLICATIONS

Manning et al., "Transient immunosuppression allows transgene expression following readministration of adeno-associated viral vectors," 1998, Human Gene Ther., 9:477-85.

Mao et al., "Persistent Suppression of Ocular Neovascularization with intravitreal administration of AAVrh. 10 coding for Bevacizumab," Hum. Gene Ther., 2011, 22:1525-35.

Nakai et al., "A limited No. of transducible hepatocytes restricts a wide-range linear vector dose response in recombinant adeno-associated virus-mediated liver transduction," J. Virol., 2002, 76:11343-9.

Nakai et al., "Unrestricted hepatocyte transduction with adeno-associated virus serotype 8 vectors in mice," J. Virol., 2005, 79:214-24.

Ncbi.nlm.nih.gov [online], "Facts and Figures Concerning the Human Retina," Jul. 5, 2007, retrieved on Mar. 28, 2020, retrieved from URL<https://www.ncbi.nlm.nih.gov/books/NBK11556/>, 6 pages.

Notredame et al., "T-Coffee: A novel method for fast and accurate multiple sequence alignment," J. Mol. Biol., 2000, 302:205-17.

Paul et al., "Determination of hepatitis E virus seroprevalence by using recombinant fusion proteins and synthetic peptides," 1994, J. Infect. Dis., 169:801-6.

PCT International Preliminary Report on Patentability in International Application No. PCT/US2016/031218, dated Nov. 16, 2017, 7 pages.

PCT International Preliminary Report on Patentability in International Application No. PCT/US2016/044819, dated Feb. 8, 2018, 5 pages.

PCT International Search Report and Written Opinion in International Application No. PCT/US2014/060163, dated Jul. 13, 2015, 19 pages.

PCT International Search Report and Written Opinion in International Application No. PCT/US2016/031218, dated Aug. 8, 2016, 12 pages.

PCT International Search Report and Written Opinion in International Application No. PCT/US2016/044819, dated Oct. 31, 2016, 5 pages.

Pettersen et al., "UCSF Chimera—a visualization system for exploratory research and analysis," 2004, J. Comp. Chem., 25:1605-12.

Reeves, "Heterogeneity in the substitution process of amino acid sites of proteins coded for by mitochondrial DNA," 1992, J. Mol. Evol., 35:17-31.

Sakhria et al., "Co-Circulation of Toscana Virus and Punique Virus in Northern Tunisia: A microneutralisation-based seroprevalence study," PLOS Negl. Trop. Dis., 2013, 7:e2429.

Santiago-Ortiz et al., "AAV ancestral reconstruction library enables selection of broadly infectious viral variants," Gene Therapy, Jul. 2015, 22: 934-946.

Sarkar et al., Abstract #: 194: "Seroprevalence Assessment of Novel, Ancestrally Derived AAV Vectors," Molecular Therapy, May 2014, 22(Supplement 1): S74.

Sauerbrei et al. "Seroprevalence of herpes simplex virus type 1 and type 2 in Thuringia, Germany, 1999 to 2006," Euro Survell., 2011, 16(44):3).

Schneider et al., "Empirical codon substitution matrix," BMC Bioinform., 2005, 6:134.

Schon et al., "Retinal gene delivery by adeno-associated virus (AAV) vectors: Strategies and applications," European Journal of Pharmaceutics and Biopharmaceutics, Jan. 2015, 95: 343-352.

Schuster et al., "Biodistribution of adeno-associated virus serotype 9 (AAV9) vector after intrathecal and intravenous delivery in mouse," Frontiers in Neuroanatomy, Jun. 2014, 8: 42 (14 pages).

Schwarz, "Estimating the Dimension of a Model," Ann. Statist. 1978, 6:461-4.

Thompson et al., "CLUSTAL W: improving the sensitivity of progressive multiple sequence alignment through sequence weighting, position-specific gap penalties and weight matrix choice," Nuc. Acids Res., 1994, 22:4673-90.

Wang et al., "Systematic Evaluation of AAV Vectors for Liver directed Gene Transfer in Murine Models," Mol. Ther., 2010, 18:118-25.

Watanabe et al., "AAVrh 10-mediated genetic delivery of bevacizumab to the pleura to provide local anti-VEGF to suppress growth of metastatic lung tumors," Gene Ther., 2010, 17:1042-51.

Whelan et al., "A general empirical model of protein evolution derived from multiple protein families using a maximum-likelihood approach," Mol. Biol. Evol., 2001, 18:691-9.

Xie et al., "AAV-mediated persistent bevacizumab therapy suppresses tumor growth of ovarian cancer," Gynecol. Oncol, 2014, 135: 325-32.

Xu et al., "Seroprevalence of herpes simplex virus types 1 and 2 in pregnant women in the United States," Am. J. Obstet. Gynecol., 2007, 196:43.e1-6.

Yang, "PAML 4: phylogenetic analysis by maximum likelihood," Mol. Biol. Evol., 2007, 24:1586-91.

Yang, "Maximum-likelihood estimation of phylogeny from DNA sequences when substitution rates differ over sites," Mol. Biol. Evol., 1993, 10:1396-1401.

Yang, "PAML: A program package for phylogenetic analysis by maximum likelihood," Comp. Applic. BioSci., 1997, 13:555-6.

Zinn and Vandenberghe, "Adeno-associated virus: fit to serve," Current Opinion in virology, Oct. 2014, 8: 90-97.

Zinn et al., "Abstract #: 237: In Silico, Ancestral Reconstruction of AAV Particles Circumvents Pre-Existing Immunity in Humans," Molecular Therapy, May 2014, 22(Supplement 1): S90.

Zinn et al., "In Silico Reconstruction of the Viral Evolutionary Lineage Yields a Potent Gene Therapy Vector," Cell Rep., Aug. 2015, 12(6):1056-1068.

Office Action in European Appln. No. 16790158.6, dated Oct. 31, 2022, 5 pages.

AU Office Action in Australian Appln. No. 2021200707, dated Sep. 10, 2021, 4 pages.

Office Action in Canadian Appln. No. 2985223, dated Mar. 21, 2023, 4 pages.

Office Action in Canadian Appln. No. 2,985,223, dated Sep. 23, 2022, 4 pages.

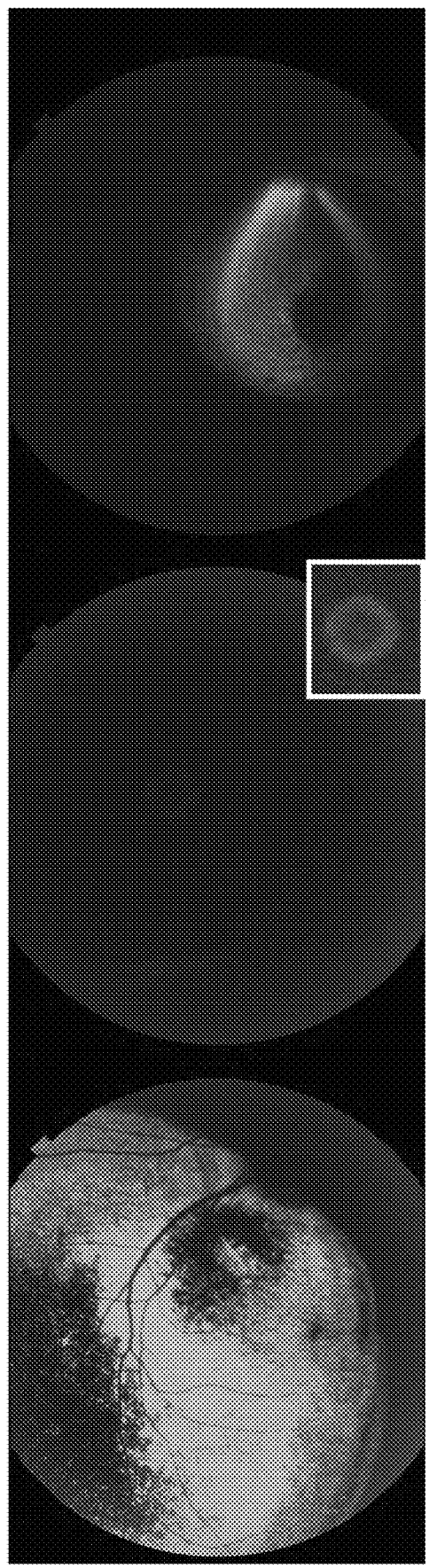

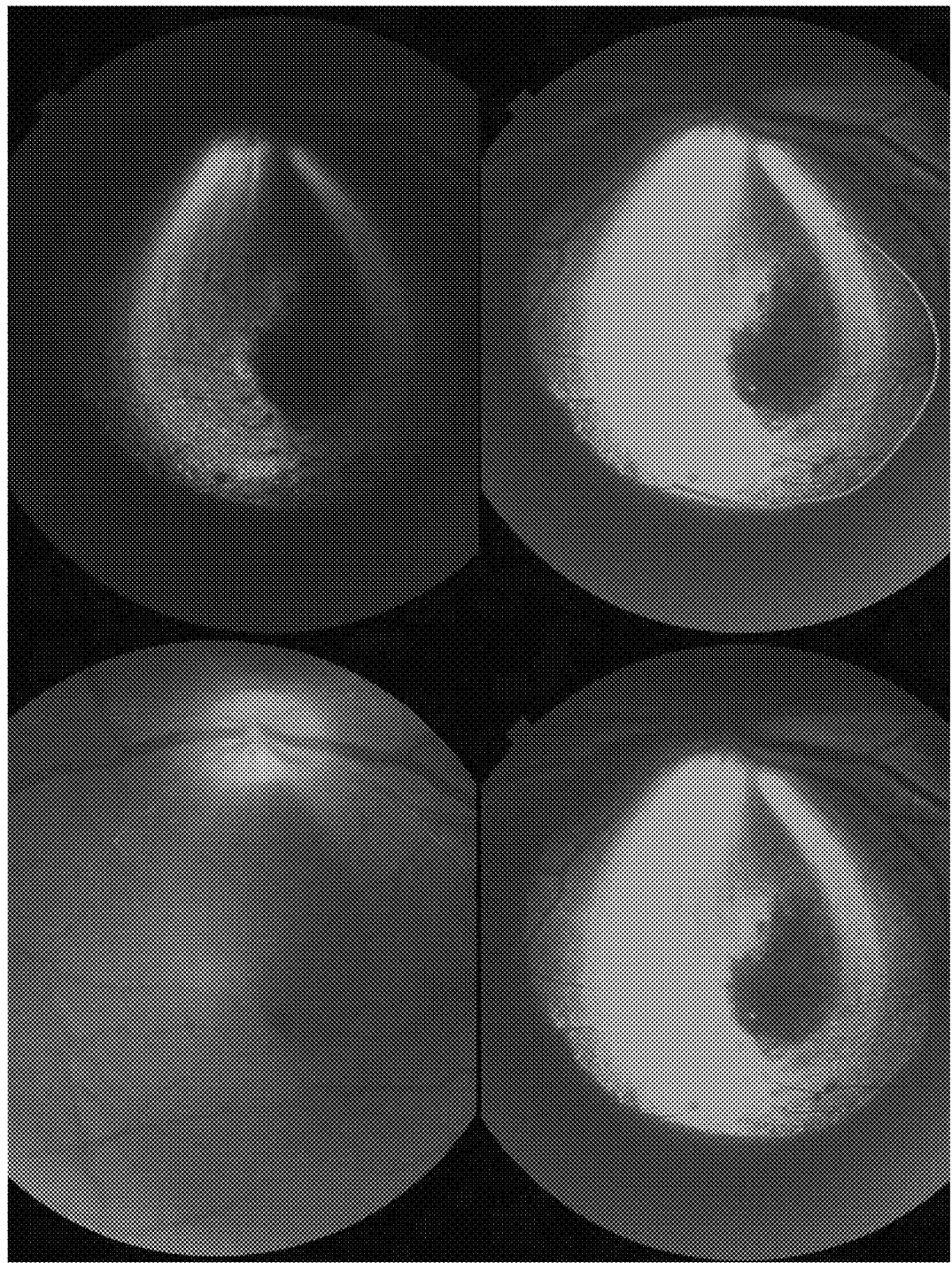

FIG. 5A
FIG. 5B
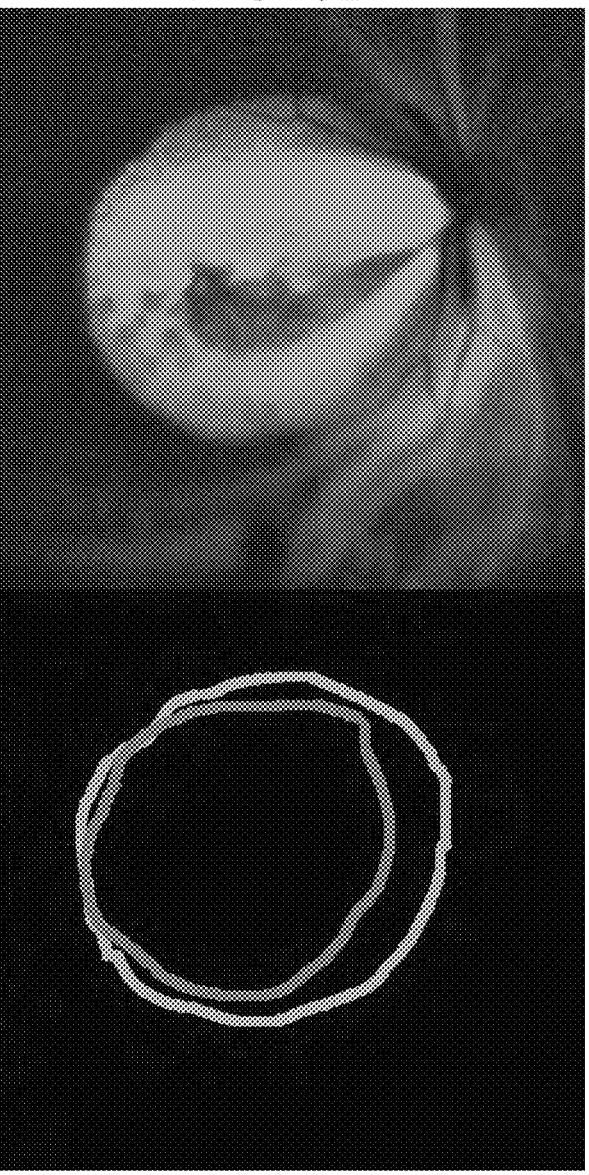
FIG. 5C
FIG. 5D

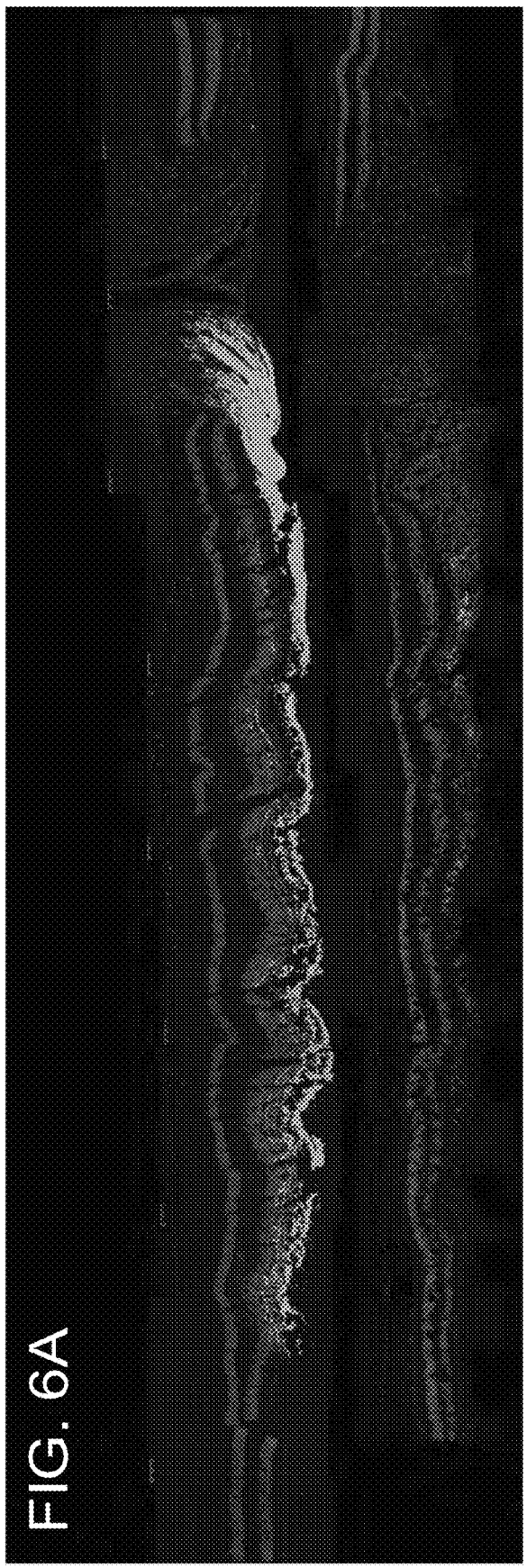
FIG. 6A
FIG. 6B

METHODS OF DELIVERING AN AGENT TO THE EYE

CROSS-REFERENCE TO RELATED APPLICATIONS

This application is a continuation of U.S. patent application Ser. No. 15/572,274, filed Nov. 7, 2017, which is a § 371 U.S. National Phase Application of International Application No. PCT/US2016/031218, filed on May 6, 2016, and claims the benefit of U.S. Application No. 62/158,393, filed on May 7, 2015. The entire contents of the foregoing are incorporated herein by reference.

TECHNICAL FIELD

This disclosure generally relates to methods of delivering an agent to the eye.

BACKGROUND

Delivering agents to the retina, and particularly to structures beyond the retina (e.g., the optic nerve), has proven challenging and has led to therapies that involve transient detachment of the retina. While certain types of transient retinal detachment seem to be well tolerated according to the vitreoretinal surgery literature, it is not known how sensitive degenerating retinas are to transient detachment. There is also concern for damage to the fovea, and it may be difficult to surgically detach the retina without causing trauma in certain disease states in which the retina is scarred to the retinal pigment epithelium (RPE) or is extensively atrophic.

In addition to the physical difficulties of transient retinal detachment, sub-retinal approaches to delivering agents have also shown limited success, e.g., in primates. For example, sub-retinal delivery of gene therapy has been unable to efficiently transduce the inner retina. For these reasons, there has been increased interest in intravitreal injections for retinal therapies. Previously published intravitreal injections have demonstrated an approximately five degree outer diameter annulus of transduction at the fovea. While improvements in the delivery vehicles have slightly increased the efficiency of gene transfer, the internal limiting membrane (ILM) has been hypothesized to be a barrier to more widespread and more efficient gene transfer.

Thus, a need still exists for a method that provides highly efficient transfer and transduction in the eye.

SUMMARY

This disclosure provides methods of delivering agents, e.g., compounds, to the eye by removing at least a portion of the inner limiting membrane (ILM) to expose a section of the retina, usually aided by removal of at least a portion of the fluid from the eye; applying a composition that includes the agent to be delivered to the exposed section of the retina; introducing a fluid replacement material, such as a gas, e.g., air or oxygen or nitrogen, or a non-aqueous liquid, e.g., silicone oil, into the eye; and maintaining the position of the compound on the exposed retina for a time sufficient to allow the agent to enter cells (e.g., 1 minute, 30 minutes), thereby delivering the agent to the retina. The methods described herein also can be used to deliver agents to other structures in the eye.

In one aspect, a method of delivering an agent to the retina is provided. Such a method typically includes: removing at least a portion of the vitreous fluid from the eye; removing at least a portion of the inner limiting membrane (ILM) to expose a section of the retina; applying a composition including an agent to the exposed section of the retina; introducing a non-diluting, fluid replacement material into the eye; and maintaining the position of the agent on the exposed retina for a time sufficient to allow the agent to enter cells in the retina; thereby delivering the agent to the retina.

In another aspect, a method of delivering an agent to a structure in the eye is provided. Such a method typically includes: removing at least a portion of an eye fluid that contacts or covers a structure in the eye to expose a section of the structure; applying a composition including an agent to the exposed section of the structure; introducing a non-diluting, fluid replacement material into the eye; and maintaining the position of the agent on the structure for a time sufficient to allow the agent to enter cells in the structure; thereby delivering the agent to the structure in the eye.

In some embodiments, the fluid from the eye is vitreous fluid. In some embodiments, the fluid from the eye is aqueous humor. In some embodiments, at least about 50% of the fluid from the eye is removed (e.g., at least about 80% of the fluid from the eye is removed). In some embodiments, the method further includes introducing a fluid detection agent into the eye prior to or during the step of removing at least a portion of the fluid from the eye. A representative fluid detection agent is triamcinolone.

In some embodiments, the portion of the ILM is surgically removed. In some embodiments, the portion of the ILM is enzymatically removed. In some embodiments, the portion of the ILM that is removed is from about 4 degrees diameter to about 40 degrees diameter. In some embodiments, the portion of the ILM that is removed is from about 0.62 mm2 to about 62 mm2. In some embodiments, the ILM is visualized with an ILM-visualization material. A representative ILM-visualization material is indocyanine green (ICG).

In some embodiments, the composition comprises a concentrated solution of the agent. In some embodiments, the composition comprises from about 50% to about 95% of the agent. In some embodiments, the composition further comprises a viscoelastic composition. In some embodiments, the agent is a viral delivery vector, a non-viral delivery vector, an antibody, a cell, a small molecule, a nanoparticle, or combinations thereof. Representative viral delivery vectors include adeno-associated virus (AAV), ancestral AAV, adenovirus, lentivirus, retrovirus, herpes simplex virus (HSV), and baculovirus. In some embodiments, the non-diluting, fluid replacement material is C3F8, SF6, air, nitrogen, oxygen, perfluoro-n-octane, or silicone oil.

In some embodiments, the maintaining step includes maintaining the position of the agent on the exposed retina for at least about 1 minute (e.g., at least about 30 minutes). In some embodiments, the maintaining step comprises maintaining the eye in a fixed position. In some embodiments, the maintaining step comprises maintaining a subject in a supine position, while in some embodiments, the maintaining step comprises maintaining a subject in a prone position.

Features of the methods described herein include that a larger area of the eye can be efficiently transduced compared to existing methods, and, for applications to the retina, detachment of the retina is not required. For example, the methods described herein can result in a significantly greater number of cells that are transduced and/or a significantly larger region of tissue that is transduced and/or more intense transduction of the cells that are transduced.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIGS. 2A to 2C are images demonstrating retinal transduction patterns in macaque following different delivery routes. Fluorescence fundus photography showed transduction patterns after subretinal (FIG. 2A), standard intravitreal (FIG. 2B), and "peel-puddle" techniques (FIG. 2C).

FIGS. 3A to 3D are images from in vivo imaging at 8 weeks after the "peel and puddle" technique using AAV2 delivered intravitreally.

FIGS. 5A to 5D are ex vivo images of the macula and surrounding regions from animal #1 using the Heidelberg Spectralis camera.

FIGS. 6A and 6B are fluorescence microscopy images showing GFP-positive signals in histological sections of the treated retinas. The optic nerve is to the right and the macula and surrounding retina is central.

DETAILED DESCRIPTION

Figure 1E:
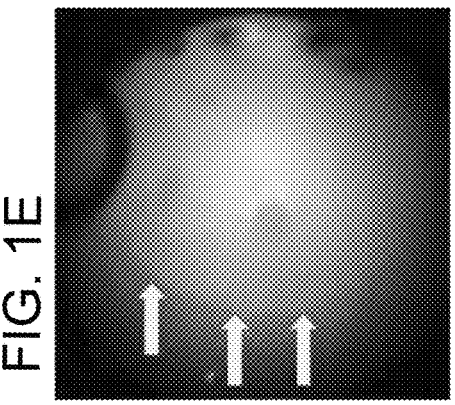
FIGS. 1A to 1D are a series of schematic diagrams that illustrate the surgical procedure for the methods described herein and FIG. 1E is a photograph of the eye during the procedure.

Methods are described herein that allow for highly efficient delivery of various agents, e.g., compounds, to the retina or another structure in the eye. As used herein, "retina" includes the inner retina and the outer retina as well as supporting and ancillary structures within the eye including, without limitation, the choroid, choriocapillaris, and retinal pigment epithelium. The methods described herein also can be used to effectively deliver an agent to other (e.g., non-retinal) structures in the eye such as the pars plana, ciliary processes, ciliary body, the iris, the lens, the trabecular meshwork, and/or the cornea or corneal endothelium.
General Methodology The methods described herein can be used to treat a variety of inherited or acquired diseases including, without limitation, retinitis pigmentosa, Stargardt disease, and macular degeneration including age-related macular degeneration. The methods described herein also can be used to treat diseases of the inner retina (such as vascular occlusions and diabetic retinopathy), diseases of the optic nerve (such as optic neuropathies and glaucoma), diseases of the anterior portion of the eye (such as corneal endothelial deficiency, cataract, ocular hypertension, and glaucoma), inflammatory diseases of the eye (such as uveitis, ocular trauma, and ocular infections), and neoplastic diseases of the eye (such as choroidal tumors, epithelial tumors, and metastatic disease).

FIGS. 1A to 1D are a series of schematic diagrams that illustrate a representative method as described herein. Simply by way of example, and as discussed in more detail below, the central vitreous is removed, e.g., using a vitrectomy hand piece (the endoscopic light source and fluid infusion cannula are not shown) (see, e.g., FIG. 1A). After visualizing the remaining vitreous, e.g., using triamcinolone crystals, suction is used to separate the posterior vitreous face from the retina and the majority of the vitreous is removed with the vitrector (see, e.g., FIG. 1B). After staining of the internal limiting membrane (ILM), e.g., with indocyanine green dye, a circular area of the ILM is peeled, e.g., with 25 gauge forceps (see, e.g., FIG. 1C). After replacing the fluid in the vitreous cavity with a fluid replacement material, e.g., air, a composition including the agent to be delivered is dripped onto the peeled area and allowed to remain in place for a sufficient time, e.g., for at least 10, 15, 20, 25, 30, 35, 45, or 60 minutes or more, depending on the nature of the composition and the agent (see, e.g., FIG. 1D).

Vitrectomy

The methods described herein can begin with a vitrectomy to remove at least a portion of the fluid from the eye (e.g., vitreous humour fluid, vitreous humour fluid including cortical vitreous, vitreous humour fluid replacements such as a balanced salt solution, or aqueous humour fluid). Depending upon the structure in the eye that is to be treated and the agent that is to be delivered, at least about 50% of the fluid in the eye can be removed (e.g., at least about 55%, 60%, 65%, or 70%), or at least about 75% of the fluid in the eye can be removed (e.g., at least about 80%, 85%, or 90%), or at least about 95% of the fluid in the eye can be removed (e.g., at least about 96%, 97%, 98%, 99%, or 100%).

Vitrectomies are known in the art, and typically utilize routine surgical equipment such as endoscopes to visualize and/or illuminate the area, cannulas to provide fluid to and/or flush the area, as well as vitrectors or vitrectomy probes, which can be used to cut up the vitreous fluid and, if connected to an appropriate pump (e.g., a venturi pump or a peristaltic pump), also can be used to remove or extract the fluid from the eye. One of the most common types of vitrectomies is a three-port vitrectomy, which includes an access port for each of an endoscope, a cannula, and a vitrector. Simply by way of example, see Jose et al., *Step By Step Vitrectomy*, 2013, Jaypee Brothers Medical Publication; and *Handbook of Vitrectomy*, 2015, Ray George, ed., ML Books International.

It would be appreciated by a skilled artisan that one or more fluid detection agents can be used to visualize the fluid in the eye, particularly when it is desirable to remove the cortical vitreous or when it is desirable to remove a great majority (e.g., essentially all) of the vitreous fluid from the eye. Fluid detection agents are known in the art and include, without limitation, triamcinolone (e.g., triamcinolone crystals), indocyanine green, and trypan blue, and BRILLIANT BLUE™. A skilled artisan would understand that a small amount of force (e.g., using suction or forceps) may be required to separate vitreous fluid from one or more interior surfaces of the eye.

It would be understood by a person of skill in the art that a vitrectomy procedure usually includes replacing the vitreous fluid of the eye with a suitable replacement material (e.g., a fluid (e.g., a vitreous) replacement material). As used herein, a suitable replacement material is non-diluting (i.e., does not result in dilution (e.g., a significant dilution) of the agent). Suitable materials that can be used to replace the fluid in the eye (e.g., the vitreous fluid) include, for example, a gas (e.g., C3F8, SF6, air, nitrogen, oxygen, and other perfluorocarbon gases), or a non-diluting liquid, e.g., a non-aqueous liquid, e.g., silicone oil, or another material (e.g., perfluoro-N-octane, PERFLUORON™) if the agent is delivered in an aqueous composition, or an aqueous fluid if the agent is delivered in a non-aqueous liquid.

While a vitrectomy is not a required step in the methods described herein, one of the main concepts of the methods described herein is that any dilution of the agent in the composition should be limited and ideally prohibited once the agent is delivered to the eye. For example, if the composition is an aqueous composition, the agent would typically be significantly diluted once the composition is administered to the vitreous or aqueous humour of the eye. By removing the vitreous and replacing it with a non-diluting replacement material, such as a gas or non-diluting liquid, one can avoid diluting the agent to be delivered.

Removing the Internal Limiting Membrane (ILM) to Treat the Retina

When the retina is the target tissue, at least a portion of the inner limiting membrane (ILM) is removed, which can be facilitated by removal of a suitable portion of the vitreous humour in the eye. A skilled artisan would appreciate that the ILM or a portion thereof can be removed prior to the vitrectomy, during or concurrently with the vitrectomy, or after completion or substantial completion of the vitrectomy. Removal of at least a portion of the ILM exposes a section of the remaining retina. The amount or area of ILM that is removed will be dependent upon the specific procedure and the structure in the eye that is targeted.

In some instances, a region of from about 4 degrees diameter to about 40 degrees diameter of the ILM is removed (e.g., from about 5 degrees diameter to about 15 degrees diameter; from about 8 degrees diameter to about 20 degrees diameter; from about 10 degrees diameter to about 35 degrees diameter; from about 15 degrees diameter to about 30 degrees diameter; or from about 20 degrees diameter to about 25 degrees diameter). In some instances, a region of from about 0.62 mm$^2$ to about 62 mm$^2$ of the ILM is removed (e.g., from about 1 mm$^2$ to about 8.8 mm$^2$; from about 0.75 mm$^2$ to about 50 mm$^2$; from about 1 mm$^2$ to about 40 mm$^2$; from about 2.5 mm$^2$ to about 35 mm$^2$; from about 5 mm$^2$ to about 25 mm$^2$; from about 7.5 mm$^2$ to about 30 mm$^2$; or from about 10 mm$^2$ to about 25 mm$^2$).

A skilled artisan would appreciate that a peeled area greater than 40 degrees or greater than 62 mm2 also can be achieved with wide angle viewing systems and/or tilting of the eye during surgery. It would be understood that treatment of a pathology localized to the macula, for example, can be accomplished by peeling the ILM over the entire macula, while pathology that extends to the peripheral retina, for example, can be accomplished by peeling a wider area extending to the peripheral retina.

The ILM can be removed using any number of known techniques and mechanisms. For example, the ILM can be surgically removed by "peeling" or "stripping" it from the retina, e.g., using forceps or other tools (e.g., 25 gauge ILM forceps, pick, scraper) or using hydro-dissection. In addition, portions of the ILM can be removed by puncturing the ILM, cutting the ILM with, for example, a laser, enzymatically digesting the ILM, or any combination thereof.

It would be appreciated by a skilled artisan that that the ILM can be visualized using an ILM-visualization agent. Visualizing the ILM can allow for improved focus on the targeted region without unnecessary damage to the remaining retina or non-targeted regions. Visualization agents include, for example, indocyanine green dye (ICG), trypan blue, and BRILLIANT BLUE™.

Application of an Agent

Following removal of at least a portion of the fluid of the eye, and following removal of at least a portion of the ILM for retinal targets, a composition can be applied to the target region (e.g., the exposed section of retina) to deliver an agent (e.g., a therapeutic agent). Agents that can be delivered to the eye include, without limitation, proteins, antibodies, cells, small molecules, nanoparticles, genome editing machinery (e.g., CRISPR/Cas9, TALEN, or zinc finger technology) or combinations thereof. In addition, agents that can be delivered to the eye for the purpose of transducing cells include, without limitation, viral delivery vectors and non-viral delivery vectors. Both types of delivery vectors are known in the art; representative viral delivery vectors include, for example, adeno-associated virus (AAV), ancestral variants of AAV (see, for example, WO 2015/054653), capsid-modified AAV, adenovirus (AV), lentivirus, retrovirus, herpes simplex virus (HSV), and baculovirus. The transduction of cells can be desirable, for example, in instances of gene replacement therapy, gene augmentation therapy, protective gene delivery, gene editing, and optogenetic therapy.

As indicated herein, it is desirable that the composition that is applied contain as much of the agent as is reasonably possible in the smallest volume reasonably possible. In other words, it is desirable that the composition contain a concentrated amount of the agent. While the actual amount of a particular agent that can be applied will depend upon the characteristics of that particular agent as well as any other components contained within the composition, it is desired that the composition that is applied contain at least about 50% of the agent (e.g., at least about 55%, 60%, 65%, 70%, 75%, 80%, 85%, 90%, 95%, or 99% of the agent) in reference to the percentage of agent itself. In addition, it is desired that the volume of the composition that is applied be, for example, no more than about 500 µl (e.g., no more than about 250 µl, 150 µl, 100 µl, or 50 µl). In some instances, the formulation of the composition can contribute to the concentration of the agent. For example, in some instances, a composition can include a low-diffusion matrix such as a viscoelastic or other adherent material or a substance that exhibits low-diffusion properties.

For optimal delivery of the agent to occur, it is often desirable to maintain the position of the agent (e.g., on the exposed retina or on a non-retina structure) for a time sufficient to allow the agent to bind to the target area and enter cells. In some embodiments, the position of the agent is maintained on the exposed retina or on a non-retina structure for at least about 1 minute (e.g., at least about 2.5 minutes, 5 minutes, 10 minutes, 12 minutes, 15 minutes, or 20 minutes), or at least about 30 minutes (e.g., at least about 45 minutes, 60 minutes, 90 minutes, 120 minutes, or longer (e.g., several hours up to several days)). This is commonly achieved by maintaining the eye in a fixed position or orientation (e.g., keeping the retina approximately horizontal) so that the composition creates a "puddle" on the target site (e.g., the exposed portion of the retina), which is kept in place by gravity. For example, depending on the structure in the eye that is targeted for delivery of an agent, a subject can be maintained in a supine position or in a prone position for the required period of time.

It would be understood by the skilled artisan that a composition that includes a viscoelastic or other adherent material, as described herein, may allow for the agent to be maintained against the target area (e.g., on the exposed retina or on a non-retina structure) without requiring the eye to be maintained in a fixed position for a period of time (e.g., without requiring the subject to remain in a supine or prone position for a period of time). In other words, the characteristics of the composition may satisfy the maintenance step described herein.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Description of Surgical Techniques

Rhesus macaques were placed under general anesthesia in a supine position. The internal limiting membrane was peeled using similar techniques to those routinely used in human macular surgery.

Figure 1B:
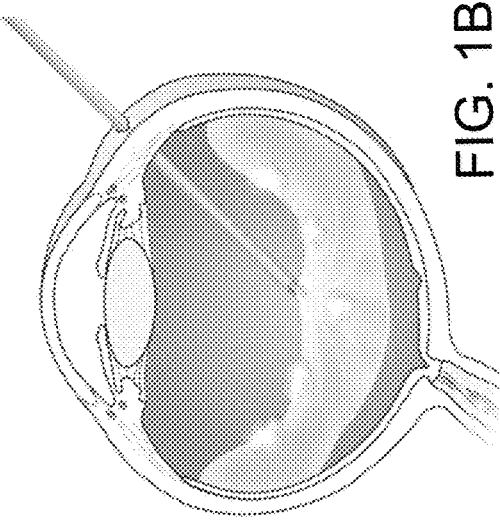
Figure 1D:
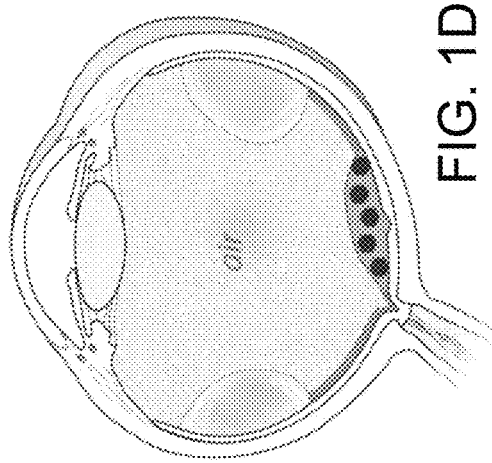
Figure 1A:
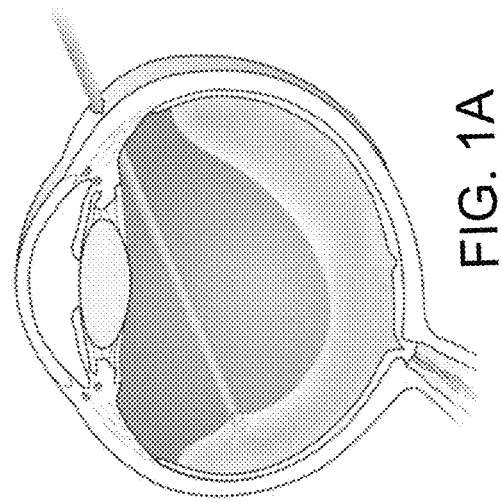
Figure 1C:
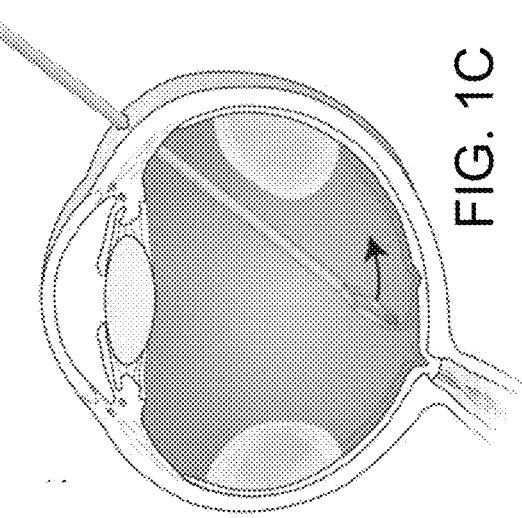

Briefly, the surgery can be summarized as follows. A vitrectomy was performed using a 25 gauge needle (FIG. 1A). TRIESENCE™ triamcinolone crystals were introduced and detachment of the posterior vitreous was induced (FIG. 1B). The ILM was stained with indocyanine green (ICG) and the internal limiting membrane (ILM) was peeled (FIG. 1C). Fluid-air exchange was performed and the virus-containing composition was positioned at the site of the peeled ILM (FIG. 1D).

The following greater detail also is provided. The eye and upper face were prepped with iodine and draped using sterile technique. All instrumentation, drugs, and surgical equipment were sterile and disposable. A standard three-port vitrectomy was performed with the Accurus vitrectomy machine and BSS+ (Alcon). See FIG. 1A. For surgical access, approximately 2 mL of saline was injected into the orbit of selected subjects with a deep orbit/brow. 25 gauge trochars (Alcon) were inserted 2.5 mm from the limbus. The fundus was visualized using a flat vitrectomy lens (DORC). After a core vitrectomy (removal of the central vitreous), Triesence triamcinolone crystals were used to visualize the remaining vitreous. Suction at the optic nerve head was used to detach the posterior hyaloid vitreous that had covered the macula and near periphery. The freed vitreous was then removed. See FIG. 1B.

After the vitrectomy, indocyanine green (ICG) was injected onto the macula to stain and visualize the internal limiting membrane (ILM). The remaining ICG was washed out and ILM forceps were used to peel the ILM using the pinch-peel technique. See FIG. 1C. A circular area was peeled, centered on the fovea and extending mid-way to the vascular arcades. A soft-tipped cannula (Alcon) and a wide-field vitrectomy lens (DORC) were used to perform a fluid-air exchange. Under air, 150 µl of concentrated virus were dripped onto the fovea to form a "puddle" in the peeled area. See FIG. 1D. The subject was allowed to remain in a supine position for 30 minutes before general anesthesia was reversed. Sub-conjunctival cefazolin and dexamethasone were administered. The air and 150 µl of fluid were left in the vitreous cavity at the end of the surgery. The air dissolved and was naturally replaced by aqueous fluid over the course of a week. FIG. 1E is a frame from a surgical video showing the edge of the peeled area in the central macula (arrows).

Example 2—Photographic Images of the Eye and Tissue Sections of the Eye

In vivo fundus photography was performed with a Topcon fundus camera and a standard color CCD camera. Fluorescein filters were used to take fluorescence images of green fluorescent protein (GFP) expression. After the subject was sacrificed, the eyes were removed and placed in 4% PFA, made into eye cups, cryopreserved in sucrose, and dissected into flat mounts. Ex vivo GFP images were acquired using a fluorescence-equipped dissecting scope with GFP and YFP filters. To co-localize the area of GFP fluorescence with the area of ILM that was peeled, we took advantage of the remaining ICG dye that stained the ILM during surgery and remained at a low level in the unpeeled area after sacrifice. The macular slice was placed in a transparent chamber and infrared, fluorescein (GFP), and ICG images were acquired using a Heidelberg Spectralis cSLO camera in ART mode. Contrast of the Spectralis images was adjusted post-processing.

Results demonstrated that subretinal injection (FIG. 2A) showed very strong fluorescence in the area of the bleb. The standard intravitreal injection (FIG. 2B) showed relatively weak fluorescence in a small area around the fovea (inset: magnified and contrast-adjusted). After the "peel & puddle" technique (FIG. 2C), relatively strong fluorescence was present in the specific area of the peel.

FIGS. 3A-D show the results of in vivo imaging at 8 weeks after using the "peel & puddle" methods and the viral vector, AAV2. Following the "peel & puddle" methods described herein, the retina had a normal appearance with fundus photography (FIG. 3A), with faint green fluorescence noted in portions of the macular nerve fiber layer. Prominent nerve fiber layer bundles were seen superiorly>inferiorly, and speckles were most prominent in the superotemporal macula using green (fluorescein) fluorescence filters (FIG. 3B). Overexposure of the image shown in FIG. 3B shows the boundaries of the fluorescence (FIG. 3C); the fovea is not fluorescent and one inferior sector of nerve fiber layer is less fluorescent than elsewhere. A portion of the border of the surgical ILM peel (red line, FIG. 3D) was traced from a frame of the surgical video; the fluorescent area corresponds to the border of the ILM peel, except that the nerve fiber layer bundles extend beyond the peeled area nasally up toward the nerve.

Figures 4A, 4B:
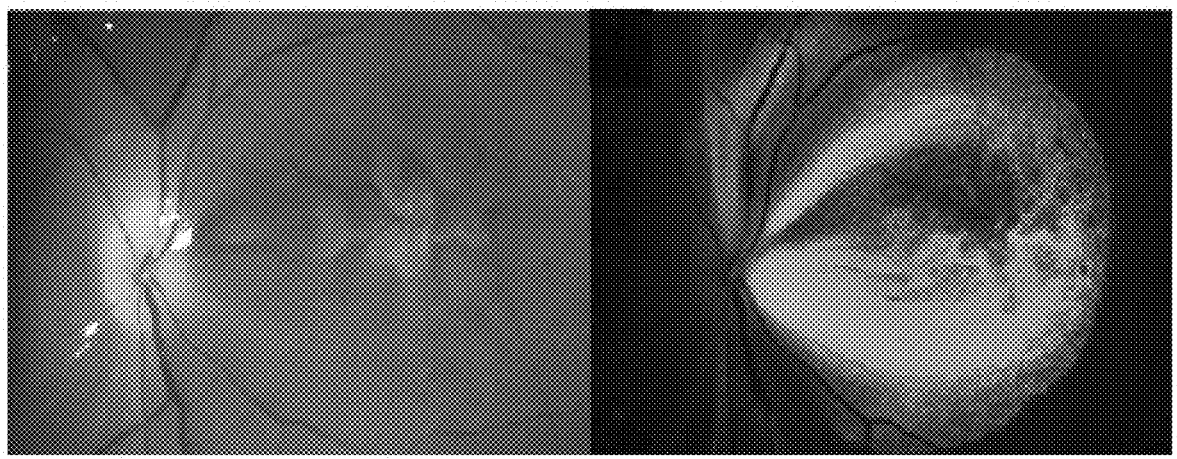
FIGS. 4A to 4F are ex vivo images at 8 to 11 weeks after surgery including fluorescence photography of the maculas of animal #1 (FIGS. 4A-4D) and animal #2 (FIGS. 4E-4F).
Figures 4C, 4D:
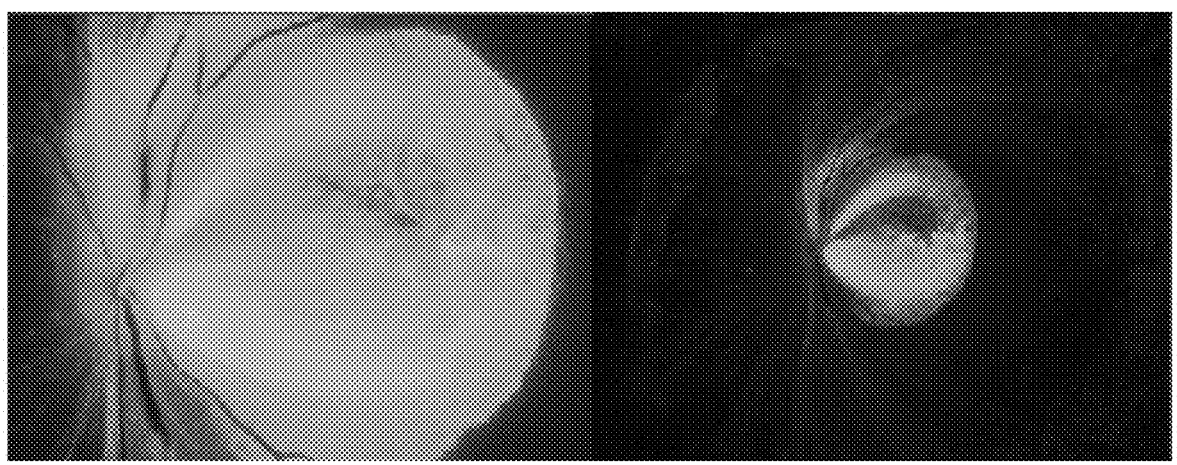
Figures 4E, 4F:
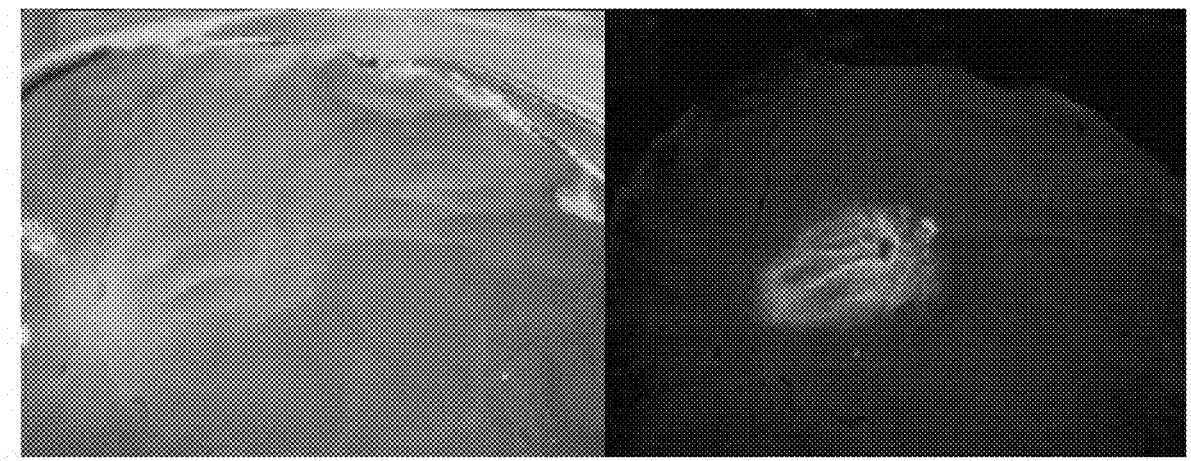

The maculas from each of animal #1 (FIGS. 4A-4D) and animal #2 (FIGS. 4E-4F) were imaged ex vivo 8 to 11 weeks after surgery. Fluorescence photos (FIGS. 4B & 4F) at the same magnification as the corresponding color photos (FIGS. 4A & 4E) demonstrated fluorescence over a large portion of the macula. Contrast enhancement of the fluorescence photo of animal #1 demonstrated the sharp border of the speckled fluorescence (FIG. 4C), and low magnification emphasized additional nerve fiber layer staining superiorly and inferiorly (FIG. 4D).

Ex vivo imaging of animal #1 on the Heidelberg Spectralis camera demonstrated the presence of residual ICG from the surgery (FIG. 5A), which revealed the precise location of the peeled area. Green fluorescence imaging is shown in FIG. 5B, and the overlay of both channels is shown in FIG. 5C. The borders of both the peeled area and the fluorescent area are in good agreement temporally, with fluorescence extending nasally beyond the peeled area (FIG. 5D).

Example 3—Histological Analysis of the Eye and Tissue Sections from the Eye

After enucleation and fixation of the eyes, the eyes were placed into sucrose, embedded and cryosectioned. Sections were stained with DAPI and photographed using DAPI and GFP filters.

FIGS. 6A-B contain fluorescence microscopy images showing GFP-positive signal in histological sections of the treated retinas. The optic nerve is to the right and the macula and surrounding retina is central. The inner retina of the macula (center) shows diffuse transduction using the peel & puddle technique (FIG. 6A) but only minimal fluorescence using the regular intravitreal technique (FIG. 6B).

Example 4—Inflammatory Responses in the Subjects

The subjects were given no post-operative steroids except for a single peri-operative subconjunctival dose of dexamethasone, which is short-acting. These surgeries were conducted as part of a cohort of surgeries which included several different sub-retinal injections as well as traditional intravitreal injections. Briefly, most of the subjects with traditional intravitreal injections also developed inflammation, and all were controlled with injections of TRIESENCE™. Almost none of the animals with sub-retinal injections developed inflammation. The first animal to develop inflammation in the larger cohort was animal #2 in this study, and, due to logistical reasons, it was decided to sacrifice the animal early rather than wait for the steroids to take effect. This prompted increased surveillance of the subjects for inflammation with portable slit-lamp exams of the anterior segment. In all further animals, inflammation was discovered at an earlier stage, and one or two steroid injections controlled the inflammation, including in animal #1 in this study.

The delayed timing of the inflammation was felt to suggest an effect of the virus (likely, the transgene) rather than of the surgery per se. In future studies, this inflammation is prevented with routine intravitreal steroid application and does not fundamentally limit the use of this technique. This is further supported by the similarity in degree of inflammation between the animals that underwent the "peel and puddle" procedure described herein and those that received traditional intravitreal injections. It is also possible that removing and/or washing out the unbound virus at the end of the 30 minute supine positioning would decrease inflammation.

OTHER EMBODIMENTS

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of delivering an agent to the retina, the method comprising:
    removing at least a portion of the vitreous fluid from the eye, and introducing a fluid detection agent into the eye prior to or during the step of removing at least a portion of the vitreous fluid from the eye;
    removing at least a portion of the inner limiting membrane (ILM) to expose a section of the retina;
    introducing a non-diluting, fluid replacement material into the eye;
    dripping a composition comprising an agent onto the exposed section of the retina; and
    maintaining the position of the agent on the exposed retina for a time sufficient to allow the agent to enter cells in the retina;
    thereby delivering the agent to the retina.

2. The method of claim 1, wherein the fluid detection agent is triamcinolone.

3. The method of claim 1, wherein the portion of the ILM is surgically or enzymatically removed.

4. The method of claim 1, wherein the portion of the ILM that is removed is from about 0.62 mm$^2$ to about 62 mm$^2$.

5. The method of claim 1, wherein the ILM is visualized with an ILM-visualization material.

6. The method of claim 5, wherein the ILM-visualization material is indocyanine green (ICG).

7. The method of claim 1, wherein the composition comprises from about 50% to about 95% of the agent.

8. The method of claim 1, wherein the composition further comprises a viscoelastic composition.

9. The method of claim 1, wherein the agent is selected from the group consisting of a viral delivery vector, a non-viral delivery vector, an antibody, a cell, a small molecule, a nanoparticle, or combinations thereof.

10. The method of claim 9, wherein the viral delivery vector is selected from the group consisting of adeno-associated virus (AAV), ancestral AAV, adenovirus, lentivirus, retrovirus, herpes simplex virus (HSV), and baculovirus.

11. The method of claim 1, wherein the non-diluting, fluid replacement material is selected from the group consisting of C3F8, SF6, air, nitrogen, oxygen, perfluoro-n-octane, and silicone oil.

12. The method of claim 1, wherein the maintaining step comprises maintaining the position of the agent on the exposed retina for at least about 30 minutes.

13. The method of claim 1, wherein the maintaining step comprises maintaining a subject in a supine or prone position.

14. A method of delivering an agent to a structure in the eye, the method comprising:
    removing at least a portion of an eye fluid that contacts or covers a structure in the eye to expose a section of the structure, and introducing a fluid detection agent into the eye prior to or during the step of removing at least a portion of the eye fluid from the eye;
    introducing a non-diluting, fluid replacement material into the eye;
    dripping a composition comprising an agent onto the exposed section of the structure; and maintaining the position of the agent on the structure for a time sufficient to allow the agent to enter cells in the structure;

thereby delivering the agent to the structure in the eye.

15. The method of claim 14, wherein the eye fluid comprises aqueous humour or vitreous fluid.

16. The method of claim 14, wherein the agent is selected from the group consisting of a viral delivery vector, a non-viral delivery vector, an antibody, a cell, a small molecule, a nanoparticle, or combinations thereof.

17. The method of claim 16, wherein the viral delivery vector is selected from the group consisting of adeno-associated virus (AAV), ancestral AAV, adenovirus, lentivirus, retrovirus, herpes simplex virus (HSV), and baculovirus.

18. The method of claim 14, wherein the non-diluting, fluid replacement material is selected from the group consisting of C3F8, SF6, air, nitrogen, oxygen, perfluoro-n-octane, and silicone oil.

* * * * *